United States Patent
Finely et al.

(10) Patent No.: US 9,775,984 B2
(45) Date of Patent: Oct. 3, 2017

(54) APPARATUS WITH UNENCAPSULATED REINFORCEMENT

(71) Applicant: Nuvectra Corporation, Plano, TX (US)

(72) Inventors: James Finely, St. Anthony, MN (US); Jesse Geroy, Ham Lake, MN (US)

(73) Assignee: NUVECTRA CORPORATION, Plano, TX (US)

( * ) Notice: Subject to any disclaimer, the term of this patent is extended or adjusted under 35 U.S.C. 154(b) by 20 days.

(21) Appl. No.: 14/813,457

(22) Filed: Jul. 30, 2015

(65) Prior Publication Data

US 2016/0030731 A1 Feb. 4, 2016

Related U.S. Application Data (60) Provisional application No. 62/032,106, filed on Aug. 1, 2014.

(51) Int. Cl.
*A61N 1/05* (2006.01)

(52) U.S. Cl.
CPC ...................................... *A61N 1/05* (2013.01)

(58) Field of Classification Search
CPC ....................................................... A61N 1/05
USPC .......................................................... 607/116
See application file for complete search history.

(56) References Cited

U.S. PATENT DOCUMENTS

| | | | |
|---|---|---|---|
| 5,231,996 A * | 8/1993 | Bardy et al. | A61N 1/056 606/108 |
| 5,702,373 A | 12/1997 | Samson | |
| 5,827,201 A | 10/1998 | Samson et al. | |
| 7,625,337 B2 | 12/2009 | Campbell et al. | |
| 8,005,549 B2 | 8/2011 | Boser et al. | |
| 8,034,045 B1 | 10/2011 | Lyons | |
| 8,644,953 B1 | 2/2014 | Finley et al. | |
| 2005/0065586 A1* | 3/2005 | Johnson | A61B 5/0422 607/122 |
| 2008/0172037 A1 | 7/2008 | Huang et al. | |
| 2013/0012923 A1 | 1/2013 | Baxter et al. | |
| 2014/0005599 A1 | 1/2014 | Sage et al. | |
| 2014/0005754 A1 | 1/2014 | Finley et al. | |
| 2014/0012357 A1 | 1/2014 | Sage et al. | |

* cited by examiner

*Primary Examiner* — Paula J Stice
(74) *Attorney, Agent, or Firm* — Haynes and Boone, LLP; Eric Li (57) ABSTRACT

In various examples, a therapy delivery element for at least partial implantation in a patient includes an elongate body. The elongate body includes a substantially tubular braided structure that extends from proximate a proximal end to proximate a distal end of the elongate body. A substantially tubular structure is coaxially disposed with respect to the braided structure. The tubular structure is attached to the braided structure proximate a distal braid end. At least a majority of the braided structure proximal from the distal braid end is unattached to the tubular structure.

20 Claims, 6 Drawing Sheets

APPARATUS WITH UNENCAPSULATED REINFORCEMENT

CROSS REFERENCE TO RELATED APPLICATIONS

This application claims the benefit of priority to U.S. Provisional Application Ser. No. 62/032,106, filed on Aug. 1, 2014, entitled "APPARATUS WITH UNENCAPSULATED REINFORCEMENT," which is incorporated by reference herein in its entirety.

BACKGROUND

The present invention relates to an apparatus with unencapsulated reinforcement, and more specifically relates to a therapy delivery element including unencapsulated reinforcement.

Various stimulation leads are used to treat various ailments including overactive bladder symptoms. Over time though, various issues have been noticed with such stimulation leads. For instance, a relatively high number of such stimulation leads that are implanted break during explant, due to, in some instances, the body forming a fibrous capsule around the stimulation lead requiring a force to remove the stimulation lead from the fibrous capsule that is greater than the stimulation lead can withstand before breaking. Breakage of the stimulation lead causes fragments of the stimulation lead to be left behind. In some cases, such fragments can migrate, become painful, and/or cause an infection. In some cases, such fragments have to be surgically removed, causing increased expense, inconvenience, pain, and/or discomfort for the patient.

Another issue is that stimulation leads often have very little ability to stretch. Additionally, over time, body tubing and/or conductor wires of the stimulation lead break down and/or lose strength. Such factors can make the body tubing and/or conductor wires susceptible to breaking under repeated cycles of flexing and/or tensile forces. A fractured conductor can no longer provide the stimulation it was intended to provide. As a result, the stimulation lead either has to be repositioned in the patient or replaced, again causing increased expense, inconvenience, pain, and/or discomfort for the patient.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used in a therapy delivery element to provide increased strength to the therapy delivery element, for instance, to inhibit breakage of the therapy delivery element during removal of the therapy delivery element from within a patient. The present inventors have further recognized, among other things, that the present subject matter, in various examples, can provide increased flexibility and/or stretch of the therapy delivery element, for instance, to allow for greater longevity under cyclic loading and/or increased body conformance. To better illustrate the apparatuses, systems, and methods described herein, a non-limiting list of examples is provided here:

Example 1 can include subject matter that can include a therapy delivery element for at least partial implantation in a patient. The therapy delivery element includes an elongate body including a proximal end and a distal end. The elongate body includes a substantially tubular braided structure including a proximal braid end and a distal braid end. The braided structure extends from proximate the proximal end of the elongate body to proximate the distal end of the elongate body. A substantially tubular structure is coaxially disposed with respect to the braided structure. The tubular structure is attached to the braided structure proximate the distal braid end. At least a majority of the braided structure proximal from the distal braid end is unattached to the tubular structure.

In Example 2, the subject matter of Example 1 optionally includes a connector proximate the proximal end of the elongate body. An electrode is proximate the distal end of the elongate body. A conductor electrically couples the electrode and the connector. The conductor extends within the braided structure between the electrode and the connector.

In Example 3, the subject matter of Example 2 is optionally configured such that the conductor is coiled within the braided structure.

In Example 4, the subject matter of Example 3 is optionally configured such that coils of the coiled conductor are substantially spirally wound along a longitudinal axis of the therapy delivery element to form a lumen within the coiled conductor.

In Example 5, the subject matter of any one of Examples 1-4 is optionally configured such that the braided structure is separated from the conductor by a gap with the therapy delivery element in a relaxed condition. The gap closes with axial stretching of the therapy delivery element. The braided structure abuts the conductor in a fully stretched condition.

In Example 6, the subject matter of any one of Examples 1-5 is optionally configured such that the tubular structure is reflowed into the braided structure proximate the distal braid end.

In Example 7, the subject matter of any one of Examples 1-6 is optionally configured such that the proximal braid end is attached proximate the tubular structure.

In Example 8, the subject matter of Example 7 is optionally configured such that the braided structure is unattached to the tubular structure between attachment points proximate the proximal braid end and the distal braid end.

In Example 9, the subject matter of any one of Examples 1-8 optionally includes at least one fixation member extending from the elongate body proximate the distal end of the elongate body. The at least one fixation member is configured to secure the therapy delivery element within the patient and to resist removal of the therapy delivery element from the patient with a force applied to the therapy delivery element of less than a removal force.

In Example 10, the subject matter of Example 9 is optionally configured such that the at least one fixation member includes at least one fin extending outwardly from the elongate body.

In Example 11, the subject matter of any one of Examples 1-10 is optionally configured such that the braided structure is configured to withstand, without breakage, an axially-applied force at least equal to a removal force.

In Example 12, the subject matter of any one of Examples 1-11 is optionally configured such that the braided structure is configured to axially stretch at least along a portion of the braided structure that is unattached to the tubular structure.

Example 13 can include, or can optionally be combined with any one of Examples 1-12 to include subject matter that can include a therapy delivery element for at least partial implantation in a patient. The therapy delivery element includes an elongate body including a proximal end and a distal end. The elongate body includes a substantially tubular braided structure including a proximal braid end and a distal braid end. The braided structure extends from proximate the proximal end of the elongate body to proximate the distal end of the elongate body. A substantially tubular structure is coaxially disposed with respect to the braided structure. The tubular structure is attached to the braided structure proximate the distal braid end. At least a majority of the braided structure proximal from the distal braid end is unattached to the tubular structure. A connector is proximate the proximal end of the elongate body. An electrode is proximate the distal end of the elongate body. A conductor electrically couples the electrode and the connector. The conductor extends within the braided structure between the electrode and the connector, wherein the braided structure is separated from the conductor by a gap with the therapy delivery element in a relaxed condition. The gap closes with axial stretching of the therapy delivery element. The braided structure abuts the conductor in a fully stretched condition. At least one fixation member extends from the elongate body proximate the distal end of the elongate body. The at least one fixation member is configured to secure the therapy delivery element within the patient and to resist removal of the therapy delivery element from the patient with a force applied to the therapy delivery element of less than a removal force, wherein the braided structure is configured to withstand, without breakage, an axially-applied force at least equal to the removal force.

In Example 14, the subject matter of Example 13 is optionally configured such that the braided structure is configured to axially stretch at least along a portion of the braided structure that is unattached to the tubular structure.

In Example 15, the subject matter of any one of Examples 13-14 is optionally configured such that the conductor is coiled within the braided structure.

In Example 16, the subject matter of Example 15 is optionally configured such that coils of the coiled conductor are substantially spirally wound along a longitudinal axis of the therapy delivery element to form a lumen within the coiled conductor.

In Example 17, the subject matter of any one of Examples 13-16 is optionally configured such that the tubular structure is reflowed into the braided structure proximate the distal braid end.

In Example 18, the subject matter of any one of Examples 13-17 is optionally configured such that the proximal braid end is attached proximate the tubular structure.

In Example 19, the subject matter of Example 18 is optionally configured such that the braided structure is unattached to the tubular structure between attachment points proximate the proximal braid end and the distal braid end.

In Example 20, the subject matter of any one of Examples 13-19 is optionally configured such that the at least one fixation member includes at least one fin extending outwardly from the elongate body.

Example 21 can include, or can optionally be combined with any one of Examples 1-20 to include subject matter that can include a therapy delivery element for at least partial implantation in a patient. The therapy delivery element includes an elongate body including a proximal end and a distal end. The elongate body includes a substantially tubular braided structure including a proximal braid end and a distal braid end. The braided structure extends from proximate the proximal end of the elongate body to proximate the distal end of the elongate body. A substantially tubular structure is coaxially disposed with respect to the braided structure. The tubular structure is attached to the braided structure proximate the distal braid end and proximate the proximal braid end. The braided structure is unattached to the tubular structure between attachment points proximate the distal braid end and the proximal braid end, wherein the braided structure is configured to axially stretch at least along a portion of the braided structure that is unattached to the tubular structure. A connector is proximate the proximal end of the elongate body. An electrode is proximate the distal end of the elongate body. A conductor electrically couples the electrode and the connector. The conductor extends within the braided structure between the electrode and the connector, wherein the braided structure is separated from the conductor by a gap with the therapy delivery element in a relaxed condition. The gap closes with axial stretching of the therapy delivery element. The braided structure abuts the conductor in a fully stretched condition. At least one fixation member extends from the elongate body proximate the distal end of the elongate body. The at least one fixation member is configured to secure the therapy delivery element within the patient and to resist removal of the therapy delivery element from the patient with a force applied to the therapy delivery element of less than a removal force, wherein the braided structure is configured to withstand, without breakage, an axially-applied force at least equal to the removal force.

In Example 22, the subject matter of Example 21 is optionally configured such that the conductor is coiled within the braided structure.

In Example 23, the subject matter of Example 22 is optionally configured such that coils of the coiled conductor are substantially spirally wound along a longitudinal axis of the therapy delivery element to form a lumen within the coiled conductor.

In Example 24, the subject matter of any one of Examples 21-23 is optionally configured such that the tubular structure is reflowed into the braided structure proximate the distal braid end.

In Example 25, the subject matter of any one of Examples 21-24 is optionally configured such that the at least one fixation member includes at least one fin extending outwardly from the elongate body.

DETAILED DESCRIPTION

The present subject matter relates to an apparatus with unencapsulated reinforcement. For instance, the apparatus of the present patent application includes, in some examples, a therapy delivery element, such as a stimulation lead, for instance, including unencapsulated reinforcement.

The present inventors have recognized, among other things, that the present subject matter can be used in a therapy delivery element to provide increased strength to the therapy delivery element, for instance, to inhibit breakage of the therapy delivery element during removal of the therapy delivery element from within a patient. The present inventors have further recognized, among other things, that the present subject matter, in various examples, can provide increased flexibility and/or stretch of the therapy delivery element, for instance, to allow for greater longevity under cyclic loading and/or increased body conformance. It should be understood, however, that the subject matter described herein can be used with other implantable medical devices, as well as an external monitor or device in some examples.

Figure 1:
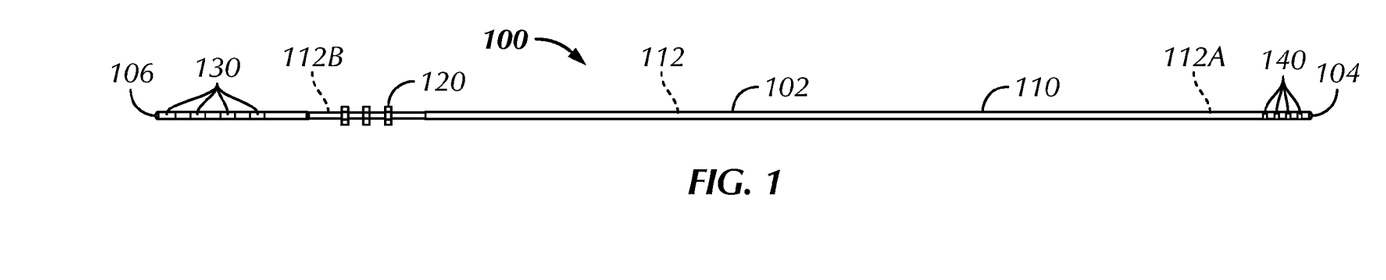
FIG. 1 is a side view of a therapy delivery element in accordance with at least one example of the invention.
Figure 2:
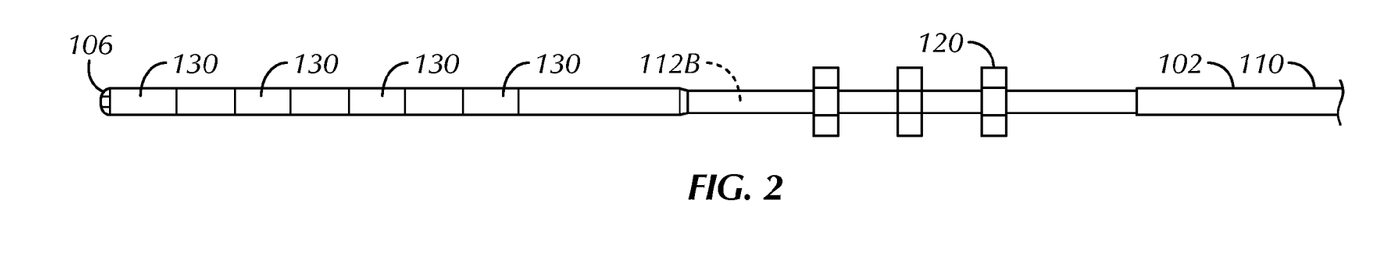
FIG. 2 is a side view of a distal end of a therapy delivery element in accordance with at least one example of the invention.
Figure 3:
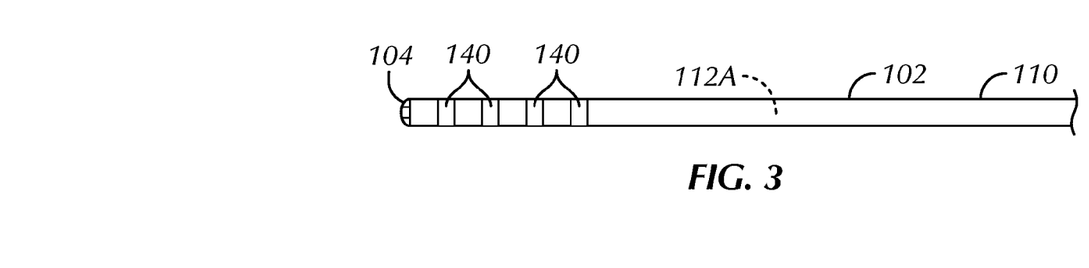
FIG. 3 is a side view of a proximal end of a therapy delivery element in accordance with at least one example of the invention.

Referring to FIG. 1, in some examples, an apparatus 100 is configured for at least partial implantation in a patient. The apparatus 100, in some examples, includes a therapy delivery element 100. In various examples, the therapy delivery element can include an electrical lead including a stimulation lead, a pacing or defibrillation lead, and/or a sensing lead. In some examples, the therapy delivery element 100 includes a fluid delivery conduit, such as a catheter, including an inner lumen that is configured to deliver a fluid, such as a pharmaceutical agent, insulin, pain relieving agent, gene therapy agent, or the like from a fluid delivery device (e.g., a fluid reservoir and/or pump) to a respective target tissue site in a patient. In some examples, the therapy delivery element can include any apparatus, device, or the like configured to provide therapy to a patient.

In some examples, the therapy delivery element 100 includes an elongate body 102 including a proximal end 104 and a distal end 106. The elongate body 102, in some examples, includes a substantially tubular braided structure 112 including a proximal braid 112A end and a distal braid end 112B. In some examples, the braided structure 112 extends from proximate the proximal end 104 to proximate the distal end 106 of the elongate body 102. In some examples, the proximal braid end 112A extends all the way to the proximal end 104 of the elongate body 102. In some examples, the distal braid end 112B extends all the way to the distal end 106 of the elongate body 102. In some examples, the proximal braid end 112A extends to a location distal from the proximal end 104 of the elongate body 102. In some examples, the distal braid end 112B extends to a location proximal from the distal end 106 of the elongate body 102. In various examples, different braid patterns can be used for the braided structure 112.

In some examples, a substantially tubular structure 110 is substantially coaxially disposed with respect to the braided structure 112. In some examples, the tubular structure 110 is disposed around at least a portion of the braided structure 112. In some examples, the tubular structure is disposed within at least a portion of the braided structure, as is described in more detail below. In some examples, the tubular structure 110 includes Urethane. In other examples, the tubular structure 110 includes one or more other materials configured to function within the therapy delivery element 100 at least partially implanted within the patient, as described herein. In some examples, the tubular structure 110 is continuous along its length. In other examples, the tubular structure is segmented along its length. That is, the tubular structure 110 can include two or more tubular structures disposed along the therapy delivery element, as is described in more detail below.

In some examples, the tubular structure 110 is attached to the braided structure at the distal braid end 112B. In some examples, at least a majority of the braided structure 112 proximal from the distal braid end 112B is unattached to the tubular structure 110. In some examples, the tubular structure 110 is reflowed into the distal braid end 112B. In some examples, the proximal braid end 112A is attached to the tubular structure 110. In some examples, the tubular structure 110 is reflowed into the proximal braid end 112A. In some examples, the braided structure 112 is unattached to the tubular structure 110 between the proximal braid end 112A and the distal braid end 112B, thereby increasing the ability of the therapy delivery element 100 to stretch. In some examples, the braided structure 112 is attached to the tubular structure 110 only at the distal braid end 112B and is otherwise unattached to the tubular structure 110, thereby further increasing the ability of the therapy delivery element 100 to stretch. In some examples, the portion of the braided structure 112 that is unattached to the tubular structure 110 rests against the tubular structure 110. In some examples, the braided structure 112 is configured to axially stretch at least along a portion of the braided structure 112 that is unattached to the tubular structure 110. In these ways, the therapy delivery element 100 can include at least one encapsulated section of the braided structure 112 (for instance, the braided structure 112 being attached to the tubular structure 110 at the distal braid end 112B and/or the proximal braid end 112A) with the remainder of the braided structure 112 being unencapsulated (for instance, the braided structure 112 being unattached to the tubular structure 110 proximal from the distal braid end 112B or between the proximal braid end 112A and the distal braid end 112B).

Various examples are contemplated herein related to what portion or portions of the braided structure 112 are attached to the tubular structure 110. For instance, in some examples, just one of the distal braid end 112B or the proximal braid end 112A is attached to the tubular structure 110, with the remainder of the braided structure 112 being unattached to the tubular structure 110. In some examples, in addition to one of the distal braid end 112B or the proximal braid end 112A being attached to the tubular structure 110, one or more portions between the distal braid end 112B and the proximal braid end 112A are attached to the tubular structure 110, with the remainder of the braided structure 112 being unattached to the tubular structure 110. In some examples, both of the distal braid end 112B and the proximal braid end 112A are attached to the tubular structure 110, with the remainder of the braided structure 112 being unattached to the tubular structure 110. In some examples, in addition to both of the distal braid end 112B and the proximal braid end 112A being attached to the tubular structure 110, one or more portions between the distal braid end 112B and the proximal braid end 112A are attached to the tubular structure 110, with the remainder of the braided structure 112 being unattached to the tubular structure 110.

Figure 4A:
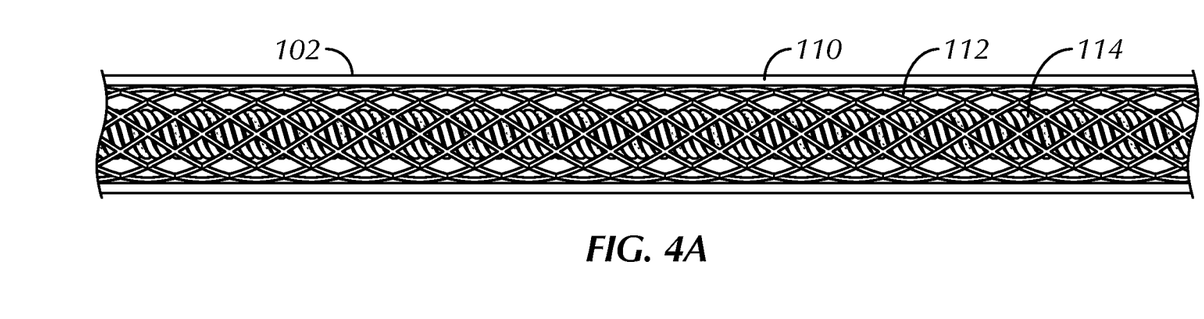
FIG. 4A is a fragmentary view of an intermediate portion of a therapy delivery element in accordance with at least one example of the invention, the therapy delivery element having a portion of a tubular structure removed.
Figure 4B:
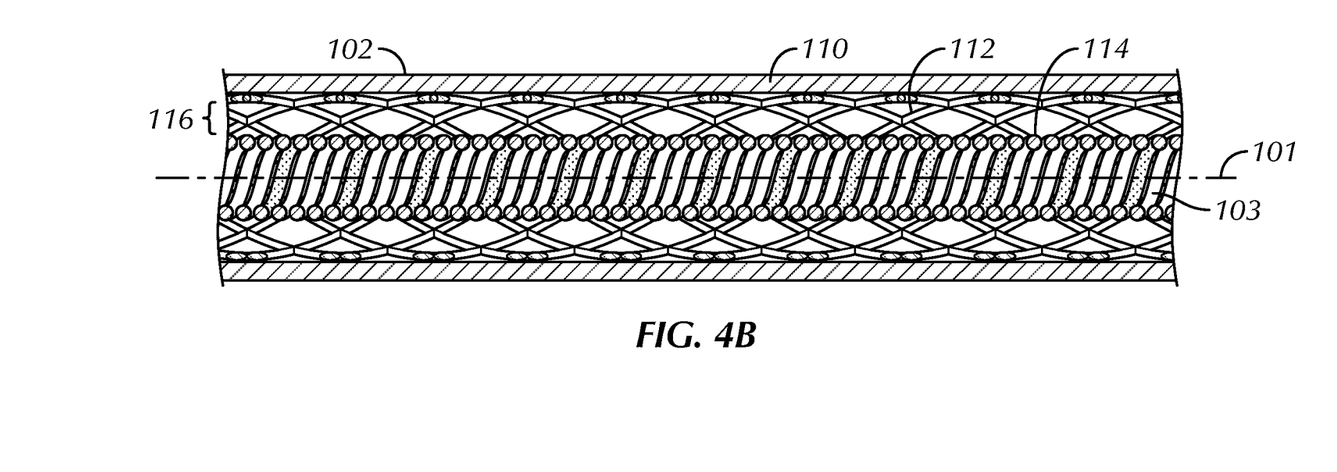
FIG. 4B is a cross-sectional view of an intermediate portion of a therapy delivery element in accordance with at least one example of the invention.
Figure 5:
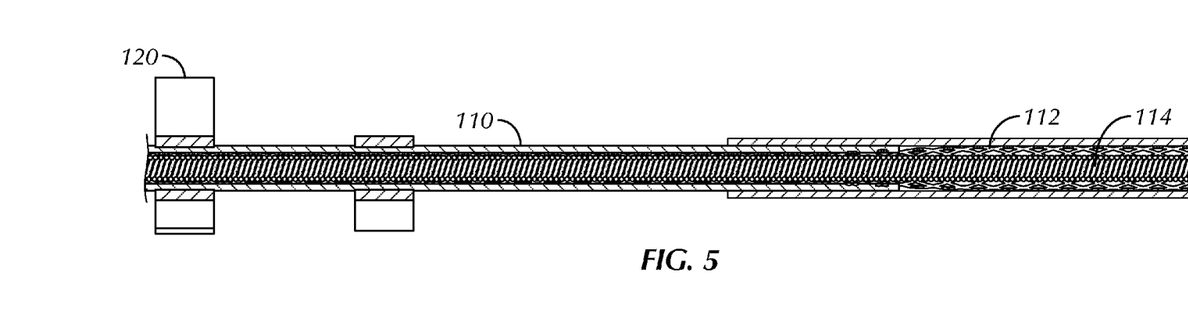
FIG. 5 is a side cross-sectional view of a distal portion of a therapy delivery element in accordance with at least one example of the invention.

In some examples, the braided structure 112 reinforces the therapy delivery element 100, for instance, to inhibit fracture of the therapy delivery element 100 during explant. In some examples, the one or more unencapsulated sections of the braided structure 112 provides for increased stretch of the therapy delivery element 100 to allow the therapy delivery element 100 to stretch, for instance, so that the therapy delivery element 100 is more compliant to tensile forces. That is, in some examples, the one or more unencapsulated sections of the braided structure 112 are free to move with respect to the tubular structure 110. In this way, in some examples, the therapy delivery element 100 can include the braided structure 112 (for instance, for tensile reinforcement) without inhibiting the ability of the therapy delivery element 100 to stretch. In some examples, once a tensile force is no longer present, natural compressive forces of one or more coiled conductors (for instance, one or more conductors 114 described below and shown in FIGS. 4A and 4B), the braided structure 112, and the tubular structure 110 can cause the braid structure 112 to return to its original size and or configuration. In this way, the therapy delivery element 110 is able to stretch and maintain a certain amount of body compliance over the life of the therapy delivery element 110.

At least one fixation member 120, in some examples, extends from the elongate body 102 proximate the distal end 106 of the elongate body 102. In some examples, the at least one fixation member 120 is configured to secure the therapy delivery element 100 within the patient and to resist removal of the therapy delivery element 100 from the patient with a force applied to the therapy delivery element 100 of less than a removal force. In some examples, the braided structure 112 is configured to withstand, without breakage, an axially-applied force at least equal to the removal force. For instance, in some examples, the one or more fixation members 120 are configured to anchor within tissue of the patient surrounding the one or more fixation members 120 to help maintain a location of the therapy delivery element 100 within the patient and/or limit unintended migration or removal of the therapy delivery element 100 from within the patient. In some examples, the tissue of the patient forms a fibrotic capsule around the one or more fixation members 120, further constraining the one or more fixation members 120 and, in turn, the therapy delivery element 100 from unintended migration or removal. In some examples, the at least one fixation member 120 includes at least one fin extending outwardly from the elongate body 102. In some examples, the one or more fixation members 120 include one or more fins extending radially outwardly from the elongate body 102. In some examples, the fixation members 120 include three sets of fixation members 120, with each set of fixation members 120 including three fins. It should be understood, however, that, in other examples, more or fewer than three sets of fixation members can be included with the therapy delivery element 100 and/or that more or fewer than three fins are included in each set of fixation members. Various examples of such fixation members are shown and described in more detail in U.S. Pat. No. 9,089,693, entitled "Lead Positioning and Finned Fixation System," which is incorporated by reference herein. In other examples, fixation members other than fins can be used, such as, but not limited to, one or more tines, one or more barbs, one or more helical anchors, or a combination of different fixation members. In some examples, proximate the distal end 106 of the elongate body 102 of the therapy delivery element 100, the tubular structure 110 and/or the braided structure 112 can be stretched down and/or reflowed together and/or reflowed into a smaller tubular structure 110, for instance, to provide an area for the one or more fixation members 120 proximal from the distal end 106 of the therapy delivery element 100.

Referring now to FIGS. 1-6B, in some examples, the therapy delivery element 100 includes a stimulation lead including one or more electrodes 130 disposed proximate the distal end 106 of the elongate body 102. In some examples, the therapy delivery element includes one or more connectors 140 proximate the proximal end 104 of the elongate body 102. In some examples, the one or more connectors 140 are configured to electrically couple with a connector of a medical device, such as an electrical stimulator device. In some examples, the proximal braid end 112A is disposed at or near the one or more connectors 140. In some examples, the proximal braid end 112A is disposed proximal to the one or more connectors 140. In other examples, the proximal braid end 112A is disposed distal to the one or more connectors 140.

In some examples, the therapy delivery element 100 includes one or more electrodes 130 proximate the distal end 106 of the elongate body 102. In some examples, the one or more electrodes 130 are configured to electrically stimulate tissue of a patient. In further examples, the one or more electrodes 130 are configured to electrically stimulate a nerve of the patient. In some examples, one or more conductors 114 electrically couple the one or more electrodes 130 and the one or more connectors 140. In some examples, the therapy delivery element 100 includes an equal number of connectors 140, electrodes 130, and conductors 114. That is, for every connector 140, there is a corresponding conductor 114 and electrode 130. In other examples, the therapy delivery element 100 includes different numbers of connectors 140, electrodes 130, and conductors 114. In some examples, the distal braid end 112B is disposed at or near the one or more electrodes 130. In some examples, the distal braid end 112B is disposed distal to the one or more electrodes 130. In other examples, the distal braid end 112B is disposed proximal to the one or more electrodes 130.

In some examples, the one or more conductors 114 extend within the braided structure 112 between the one or more electrodes 130 and the one or more connectors 140. In some examples, the one or more conductors 114 are coiled within the braided structure 112. In some examples, coils of one or more coiled conductors 114 are substantially spirally wound along a longitudinal axis 101 of the therapy delivery element 100 to form a lumen 103 within the one or more coiled conductors 114. In some examples, the lumen 103 is sized to accommodate a stylet or another device within the lumen 103. In some examples, the braided structure 112 is separated from the one or more conductors 114 by a gap 116 with the therapy delivery element 100 in a relaxed condition. In some examples, the gap 116 closes with axial stretching of the therapy delivery element 100. In some examples, the braided structure 112 abuts the one or more conductors 114 (such that there is no gap 116 between the braided structure 112 and the one or more conductors 114) in a fully stretched condition. In some examples, the tubular structure 110 includes an inner diameter that is significantly larger than an outer diameter of the one or more conductors 114 to provide the gap 116 for the braided structure 112 to stretch and/or neck down in, for instance, if the therapy delivery element 100 is pulled on.

Figure 6A:
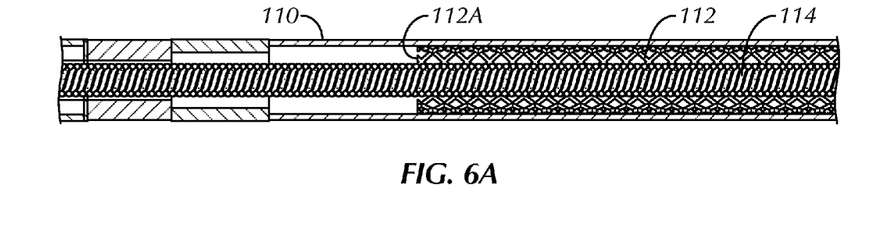
FIG. 6A is a side cross-sectional view of a proximal portion of a therapy delivery element in accordance with at least one example of the invention.
Figure 6B:
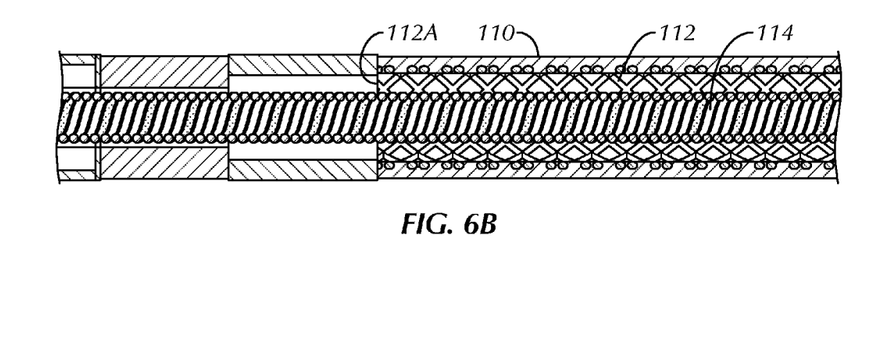
FIG. 6B is a side cross-sectional view of a proximal portion of a therapy delivery element in accordance with at least one example of the invention.
Figure 7A:
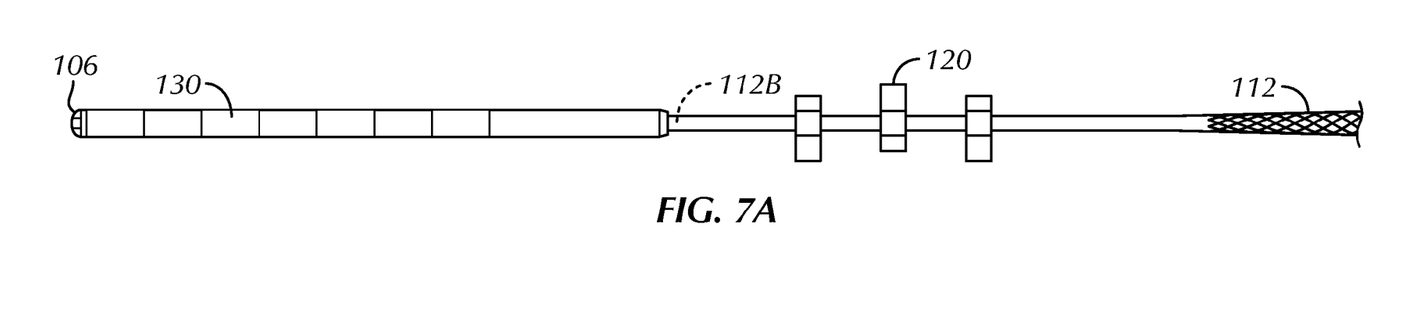
FIG. 7A is a side view of a distal end of a therapy delivery element in accordance with at least one example of the invention.
Figure 7B:
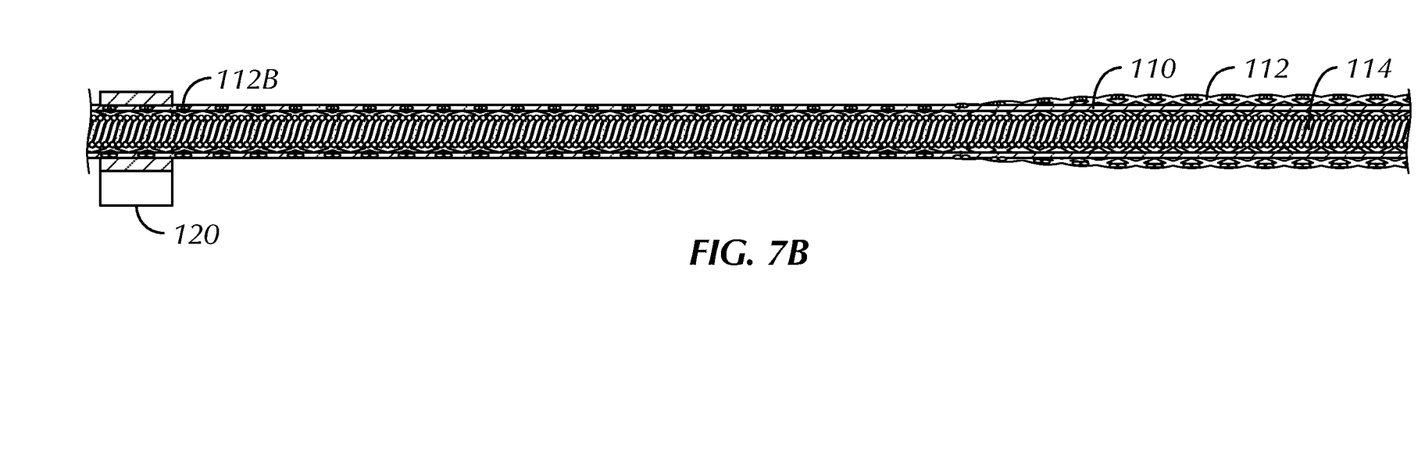
FIG. 7B is a side cross-sectional view of a distal portion of a therapy delivery element in accordance with at least one example of the invention.

Referring to FIGS. 6A and 6B, in various examples, as described above, the proximal braid end 112A can be unattached to the tubular structure 110 (FIG. 6A) or attached to the tubular structure 110 (FIG. 6B).

For instance, in the example shown in FIG. 6A, the tubular structure 110 is disposed around the braided structure 112, but there are no attachments of the braided structure 112 near the proximal braid end 112A to the tubular structure 110. That said, in some examples, the braided structure 112 can be configured to expand outwardly against an interior of the tubular structure 110, potentially forming a frictional engagement, but no more substantial attachment is formed, such as by reflowing the tubular structure 110 into the braided structure 112, using adhesive, or using some other form of attachment.

In other examples, however, such as the example shown in FIG. 6B, the proximal braid end 112A of the braided structure 112 is attached to the tubular structure 110. In some examples, the tubular structure 110 is reflowed into the proximal braid end 112A of the braided structure 112 (portions of the braided structure 112 are shown at least partially reflowed or encased in the tubular structure 110). In other examples, other forms of attachment can be used between the tubular structure 110 and the proximal braid end 112A of the braided structure 112, such as adhesive, epoxy, or the like.

Although shown in FIG. 1 as being continuous along the length of the therapy delivery element 100, in some examples, the tubular structure 110 can be segmented. That is, the tubular structure 110 can actually include one or more shorter segments. In some examples, the one or more segments do not extend the entire length of the therapy delivery element 100, such that one or more portions of the braided structure 112 are not covered by the tubular structure 110. For instance, in some examples, the tubular structure 110 includes a distal segment only, the distal segment being at least partially attached (reflowed or otherwise) to the braided structure 112. In other examples, the tubular structure 110 includes a distal segment and a proximal segment, with each of the distal and proximal segments being at least partially attached (reflowed or otherwise) to the braided structure 112. In still other examples, the tubular structure 110 includes more than two segments that are at least partially attached (reflowed or otherwise) to the braided structure 112.

Referring now to FIGS. 7A-9B, in some examples, the braided structure 112 can be disposed around the tubular structure 110. As seen in FIG. 7B, the tubular structure 110 is disposed between the braided structure 112 and the one or more conductors 114. In some examples, the distal braid end 112B of the braided structure 112 is attached to the tubular structure 110 in the vicinity of the one or more fixation members 120. In some examples, the tubular structure 110 is reflowed into the distal braid end 112B of the braided structure 112 to attach the tubular structure 110 to the braided structure 112.

Figure 8A:
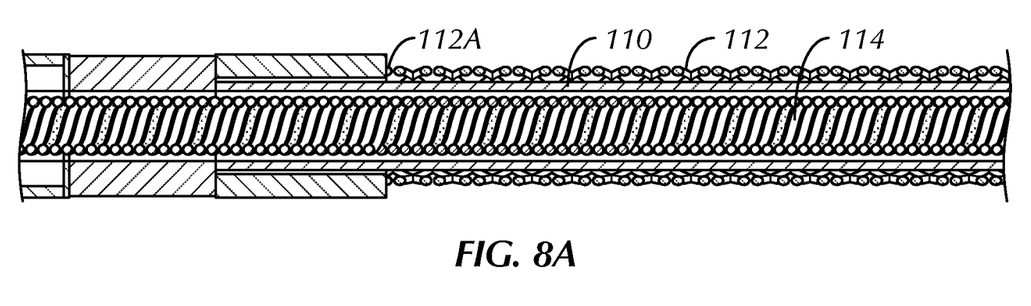
FIG. 8A is a side cross-sectional view of a proximal portion of a therapy delivery element in accordance with at least one example of the invention.
Figure 8B:
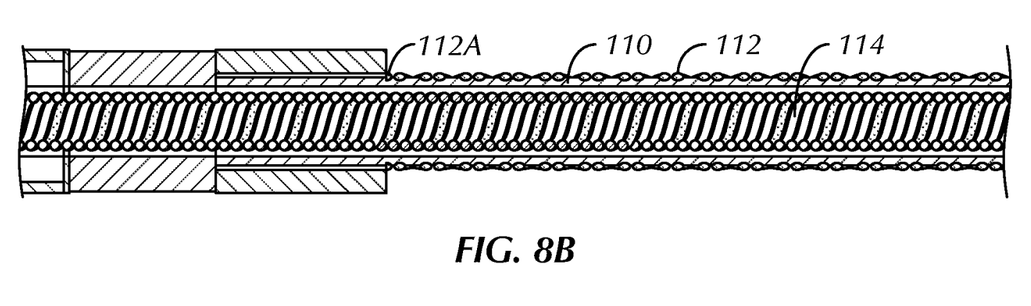
FIG. 8B is a side cross-sectional view of a proximal portion of a therapy delivery element in accordance with at least one example of the invention.

Referring to FIGS. 8A and 8B, in various examples, the proximal braid end 112A can be unattached to the tubular structure 110 (FIG. 8A) or attached to the tubular structure 110 (FIG. 8B). For instance, in the example shown in FIG. 8A, the tubular structure 110 is disposed within the braided structure 112, but there are no attachments of the braided structure 112 near the proximal braid end 112A to the tubular structure 110. That is, in some examples, no substantial attachment is formed, such as by reflowing the tubular structure 110 into the braided structure 112, using adhesive, or using some other form of attachment. In other examples, however, such as the example shown in FIG. 8B, the proximal braid end 112A of the braided structure 112 is attached to the tubular structure 110. In some examples, the tubular structure 110 is reflowed into the proximal braid end 112A of the braided structure 112 (portions of the braided structure 112 are shown at least partially reflowed or encased in the tubular structure 110). In other examples, other forms of attachment can be used between the tubular structure 110 and the proximal braid end 112A of the braided structure 112, such as adhesive, epoxy, or the like.

Figure 9A:
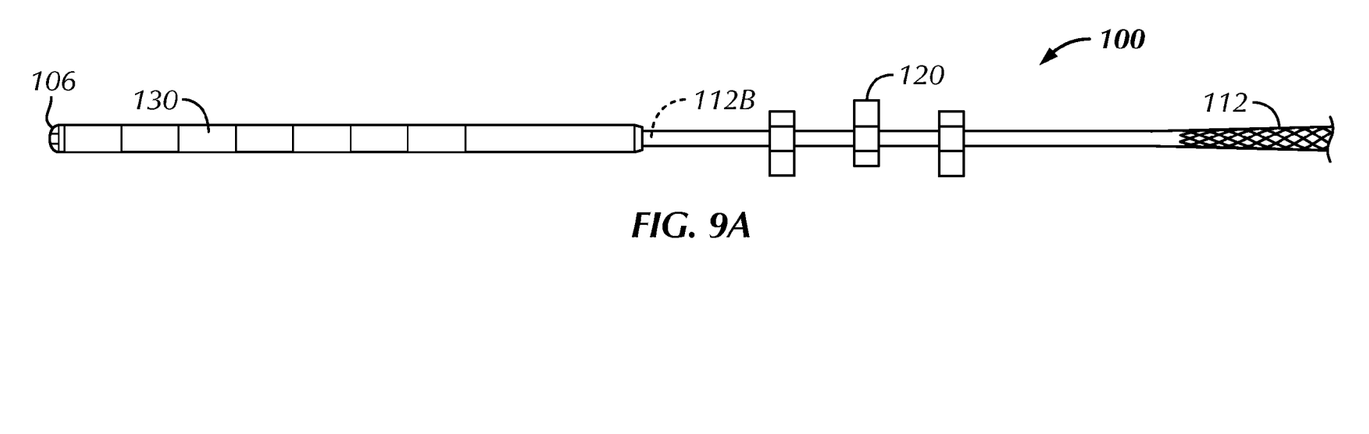
FIG. 9A is a side view of a distal end of a therapy delivery element in accordance with at least one example of the invention.
Figure 9B:
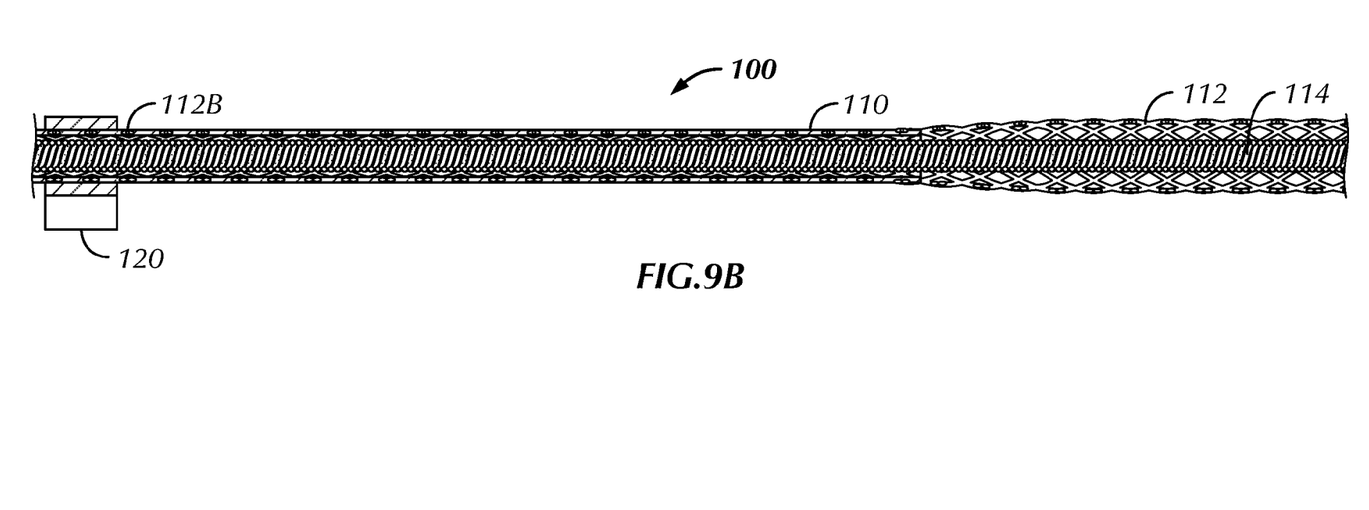
FIG. 9B is a side cross-sectional view of a distal portion of a therapy delivery element in accordance with at least one example of the invention.

Referring now to FIGS. 9A and 9B, in some examples, the tubular structure 110 can be segmented. That is, the tubular structure 110 can actually include one or more shorter segments. In some examples, the one or more segments do not extend the entire length of the therapy delivery element 100, such that one or more portions of the braided structure 112 do not include the tubular structure 110 within the braided structure 112. For instance, in some examples and as seen in FIGS. 9A and 9B, the tubular structure 110 includes a distal segment extending under the one or more fixation members 120 and extending a distance proximally along the therapy delivery element 100, the distal segment being at least partially attached (reflowed or otherwise) to the braided structure 112. In other examples, the tubular structure 110 includes a distal segment and a proximal segment, with each of the distal and proximal segments being at least partially attached (reflowed or otherwise) to the braided structure 112. In still other examples, the tubular structure 110 includes more than two segments that are at least partially attached (reflowed or otherwise) to the braided structure 112.

In some examples, in use, the therapy delivery element 110 can be implanted with the use of an introducer assembly and tunneled to an implantable pulse generator. When the therapy delivery element 100 is to be removed, in some examples, the physician or other user can make an incision near an implantation site or near a pocket where the implantable generator resides, and the physician or other user can grab the therapy delivery element 100 and pull. In doing so, in some examples, the braided structure 112 can reinforce the therapy delivery element 100 as the therapy delivery element 100 is removed and increase the likelihood that an entirety of the therapy delivery element 100 is explanted.

The present inventors have recognized various advantages of the subject matter described herein. For instance, in some examples, the therapy delivery element described herein can exhibit increased strength, for instance, to inhibit breakage of the therapy delivery element during removal of the therapy delivery element from within a patient. In some examples, the therapy delivery element described herein can include increased flexibility and/or ability to stretch, for instance, to allow for greater longevity under cyclic loading and/or increased body conformance of the therapy delivery element. In some examples, the therapy delivery element 100 can incorporate the use of reinforcement of the therapy delivery element 100 from the braided structure 112 throughout the length of the therapy delivery element 100 while still allowing the therapy delivery element 100 to stretch, for instance, to be body compliant. That is, in some examples, the braided structure 112 helps to strengthen the therapy delivery element 100 and enables the therapy delivery element 100 to withstand a higher load, for instance, when being removed. In some examples, since the majority of the braided structure 112 is free to move, the therapy delivery element 100 is able to have a relatively high level of stretchiness. This is believed to be advantageous, in some examples, because the therapy delivery element 100 can be less prone to fracture during explant and can be more body compliant. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A therapy delivery element for at least partial implantation in a patient, the therapy delivery element comprising:
   an elongate body including a proximal end and a distal end, wherein the elongate body includes:
   a tubular braided structure including a proximal braid end and a distal braid end, the braided structure extending from proximate the proximal end of the elongate body to proximate the distal end of the elongate body;
   a conductor extending within the braided structure; and
   a tubular structure coaxially disposed with respect to the braided structure, the tubular structure being attached to the braided structure proximate the distal braid end, at least a majority of the braided structure proximal from the distal braid end being unattached to the tubular structure;
   wherein the braided structure abuts the conductor when the therapy delivery element is in a fully stretched condition but does not abut the conductor when the therapy delivery element is in a relaxed condition; and
   wherein when the therapy delivery element is in the relaxed condition, a separation of the braided structure from the conductor consists of a gap.

2. The therapy delivery element of claim 1, comprising:
   a connector proximate the proximal end of the elongate body; and
   an electrode proximate the distal end of the elongate body;
   wherein the conductor electrically couples the electrode to the connector.

3. The therapy delivery element of claim 1, wherein the conductor is a coiled conductor that is coiled within the braided structure.

4. The therapy delivery element of claim 3, wherein coils of the coiled conductor are spirally wound along a longitudinal axis of the therapy delivery element to form a lumen within the coiled conductor.

5. The therapy delivery element of claim 1, wherein the gap completely disappears with full axial stretching of the therapy delivery element.

6. The therapy delivery element of claim 1, wherein the braided structure is configured to expand outwardly against an interior of the tubular structure to form a frictional engagement.

7. The therapy delivery element of claim 1, wherein the braided structure is unattached to the tubular structure between attachment points proximate the proximal braid end and the distal braid end.

8. The therapy delivery element of claim 1, comprising at least one fixation member extending from the elongate body proximate the distal end of the elongate body, the at least one fixation member being configured to secure the therapy delivery element within the patient and to resist removal of the therapy delivery element from the patient with a force applied to the therapy delivery element of less than a remove force.

9. The therapy delivery element of claim 8, wherein the at least one fixation member includes at least one fin extending outwardly from the elongate body.

10. The therapy delivery element of claim 1, wherein the braided structure is configured to withstand, without breakage, an axially-applied force at least equal to a removal force.

11. The therapy delivery element of claim 1, wherein the braided structure is configured to axially stretch at least along a portion of the braided structure that is unattached to the tubular structure.

12. The therapy delivery element of claim 1, wherein the tubular structure is segmented, and wherein some segments of the braided structure are not covered by the tubular structure.

13. A therapy delivery element for at least partial implantation in a patient, the therapy delivery element comprising:
an elongate body including a proximal end and a distal end, wherein the elongate body includes:
a tubular braided structure including a proximal braid end and a distal braid end, the braided structure extending from proximate the proximal end of the elongate body to proximate the distal end of the elongate body; and
a tubular structure coaxially disposed with respect to the braided structure, the tubular structure being attached to the braided structure proximate the distal braid end, at least a majority of the braided structure proximal from the distal braid end being unattached to the tubular structure;
a connector proximate the proximal end of the elongate body;
an electrode proximate the distal end of the elongate body;
a conductor electrically coupling the electrode and the connector, the conductor extending within the braided structure between the electrode and the connector, wherein the braided structure is separated from the conductor only by a gap with the therapy delivery element in a relaxed condition, the gap closing with axial stretching of the therapy delivery element, the braided structure abutting the conductor in a fully stretched condition; and
at least one fixation member extending from the elongate body proximate the distal end of the elongate body, the at least one fixation member being configured to secure the therapy delivery element within the patient and to resist removal of the therapy delivery element from the patient with a force applied to the therapy delivery element of less than a removal force, wherein the braided structure is configured to withstand, without breakage, an axially-applied force at least equal to the removal force.

14. The therapy delivery element of claim 13, wherein the braided structure is configured to axially stretch at least along a portion of the braided structure that is unattached to the tubular structure.

15. The therapy delivery element of claim 13, wherein the braided structure is configured to expand outwardly against an interior of the tubular structure to form a frictional engagement.

16. The therapy delivery element of claim 13, wherein the proximal braid end is attached proximate the tubular structure.

17. The therapy delivery element of claim 16, wherein the braided structure is unattached to the tubular structure between attachment points proximate the proximal braid and the distal braid end.

18. A therapy delivery element for at least a partial implantation in a patient, the therapy delivery element comprising:
an elongate body including a proximal end and a distal end, wherein the elongate body includes:
a tubular braided structure including a proximal braid end and a distal braid end, the braided structure extending from proximate the proximal end of the elongate body to proximate the distal end of the elongate body; and
a tubular structure coaxially disposed with respect to the braided structure, the tubular structure being attached to the braided structure proximate the distal braid end, the braided structure being unattached to the tubular structure between attachment points proximate the distal braid end and the proximal braid end, wherein the braided structure is configured to axially stretch at least along a portion of the braided structure that is unattached to the tubular structure;
a connector proximate the proximal end of the elongate body;
an electrode proximate the distal end of the elongate body;
a conductor electrically coupling the electrode and the connector, the conductor extending within the braided structure between the electrode and the connector, wherein the braided structure is separated from the conductor only by a gap with the therapy delivery element in a relaxed condition, the gap completely disappearing with full axial stretching of the therapy delivery element, the braided structure abutting the conductor in a fully stretched condition; and
at least one fixation member extending from the elongate body proximate the distal end of the elongate body, the at least one fixation member being configured to secure the therapy delivery element within the patient and to resist removal of the therapy delivery element from the patient with a force applied to the therapy delivery element of less than a removal force, wherein the braided structure is configured to withstand, without breakage, an axially-applied force at least equal to the removal force.

19. The therapy delivery element of claim 18, wherein the conductor is coiled within the braided structure, and wherein coils of the conductor are spirally would along a longitudinal axis of the therapy delivery element to form a lumen within the coiled conductor.

20. The therapy delivery element of claim 18, wherein the braided structure is configured to expand outwardly against an interior of the tubular structure to form a frictional engagement.

* * * * *

UNITED STATES PATENT AND TRADEMARK OFFICE
CERTIFICATE OF CORRECTION

PATENT NO.       : 9,775,984 B2
APPLICATION NO.  : 14/813457
DATED            : October 3, 2017
INVENTOR(S)      : James Finley and Jesse Geroy Page 1 of 1

It is certified that error appears in the above-identified patent and that said Letters Patent is hereby corrected as shown below:

On the Title Page

Item (12), delete "Finely" and insert --Finley--

Item (72), delete "Finely" and insert --Finley--

Signed and Sealed this
Twentieth Day of February, 2018

Andrei Iancu
*Director of the United States Patent and Trademark Office*